United States Patent [19]

Setälä et al.

[11] Patent Number: 5,053,233
[45] Date of Patent: Oct. 1, 1991

[54] FORAGE PRESERVATION

[75] Inventors: Jouko J. Setälä, Helsinki; Veli M. S. Suominen, Hyvinkää; Aino L. Rauramaa, Espoo; Seppo Sivelä, Helsinki, all of Finland

[73] Assignee: Valio Meijerien Keskusosuusliike, Finland

[21] Appl. No.: 424,980

[22] Filed: Oct. 23, 1989

[30] Foreign Application Priority Data

Nov. 14, 1988 [FI] Finland ................................ 885252

[51] Int. Cl.$^5$ ............................................... A23K 1/00
[52] U.S. Cl. ............................................. 426/53; 426/52; 426/61; 426/636; 426/807; 435/857
[58] Field of Search ..................... 426/52, 53, 54, 623, 426/630, 636, 335, 532, 807; 435/857

[56] References Cited

U.S. PATENT DOCUMENTS

| | | | |
|---|---|---|---|
| 4,528,199 | 7/1985 | Moon et al. | 426/53 |
| 4,751,089 | 6/1988 | Heikonen | 426/53 |
| 4,820,531 | 4/1989 | Tomes | 426/53 |
| 4,842,871 | 6/1989 | Hill | 426/53 |

FOREIGN PATENT DOCUMENTS

A336734 11/1971 European Pat. Off. .
A250786 2/1987 European Pat. Off. .

OTHER PUBLICATIONS

The Merck Index Published by Merck Co. Inc., Eighth Edition (1968), p. 98.
"The Antimicrobial Spectra of Some Salts of Organic Acids and Glutaraldehyde in Respect to Their Potential as Silage Additives", M. K. Woolford, Grass and Forage Science, vol. 39, pp. 53–57, 1984.

Primary Examiner—R. B. Penland
Attorney, Agent, or Firm—Finnegan, Henderson, Farabow, Garrett & Dunner

[57] ABSTRACT

The invention relates to a process of preserving forage, a *Lactobacillus plantarum* strain used in the process, the use of the strain in the preservation of forage, and forage preserved according to the invention. The bacterial strain is preferably used in combination with at least one other preservative, such as cellulase and oragnic acid and/or in combination with at least one other lactic acid bacterium.

21 Claims, 1 Drawing Sheet

FORAGE PRESERVATION

This invention relates to a process of preserving forage, a *Lactobacillus plantarum* strain used in the process, the use of the strain in the preservation of forage, and forage preserved according to the invention.

In the preservation of forage, such as grass, chopped forage prepared from grass is sealed air-tightly in a silo so as to ferment the carbohydrates contained in the grass (mainly glucose, fructose and fructosans) into acids. Under favourable conditions, such fermentation processes produce mainly lactic acid. This provides silage of high quality with low fermentation losses. In general, fermentation also produces volatile fatty acids, such as acetic acid, in the forage. All the fermentation acids reduce the pH of silage. As is well known, preservation of forage requires that its pH should be reduced to 4 or even lower, which requires about 100 acid equivalents per one ton of forage.

Free fermentation occurring in forage is difficult to control towards desired fermentation, that is, towards lactic acid fermentation as pure as possible. For this reason, attempts have been made to achieve improved forage preservation by preservatives. The best known amongst these methods is the principle introduced by A. I. Virtanen, called AIV principle, according to which either organic or inorganic acids are added to the forage separately or as a mixture. Acid(s) is(are) added to the forage in an amount sufficient to reduce the pH of the forage to 4 or below. Formic acid alone or in combination with other acids is today used in most cases. Other preservatives include those disclosed, e.g., by Vanbelle and Bertin (see Ensilage—new biological aspects, Sanofi Sante Animale, 1985). Preservatives having a direct inhibitory effect on fermentation include those containing formalin. Examples of these are to be found, e.g., in the above reference as well as in Finnish Patent Specification 68949.

However, the use of acids and acid-formalin mixtures involves problems such as the corrosiveness typical of acids and the allergic symptoms caused by formalin. Therefore attempts have been made to introduce preservatives which do not have such disadvantageous properties. Alternative agents used include plant fibre degrading enzymes (e.g., Finnish Patent 66282). Such enzymes produce extra sugars in the forage for use as raw material in the fermentation caused by the microflora present in grass. Since the microflora present in grass is very heterofermentative, a mere production of sugar is not sufficient to ensure high quality of forage and low storage losses (e.g., Setälä, Enzymes in the forefront of food and feed industries, Seminar at Espoo/Otaniemi, June 16—June 17, 1988). In an attempt to avoid the problem caused by the heterofermentativeness of the microflora, mostly homofermentative lactic acid bacteria have been added to the forage concurrently with the enzyme addition. The use and testing of such lactic acid bacteria have been described, e.g., by Woolford and Sawczyc (see Grass and Forage Science 39 (1984) 139–158). The use of certain bacterial strains has also been suggested for forage preservation (EP-A2-0 250 786). In most cases, the origin of the strains, their behaviour under silo conditions, and the properties of the strains have been identified and disclosed indistinctly in the publications in question, wherefore the tests performed on the different strains on the basis of the data obtained from the publications have had poor results, also in terms of the quality of silage.

Different researchers have applied greatly varying criteria for inoculant bacteria to be used in preserving forage. In general, the most important criteria have included:
good growth over a wide temperature range and under both aerobic and anaerobic conditions;
homofermentativeness;
acid tolerance;
rapid production of acid;
lack of proteolytic activity;
ability to ferment glucose, fructose, sucrose;
does not produce dextran from sucrose nor mannitol from fructose;
active over a wide dry matter range; and
stable properties.

Side fermentation in silage is attempted to be prevented by a preservative which should not affect the homofermentative lactic acid bacterium used and its properties. The best known of the preservatives is formic acid. However, it has not been possible to use formic acid in combination with lactic acid bacteria because the acid as such restricts bacterial activity.

It has been found unexpectedly that it is possible to isolate from silage a highly active and formiate-tolerant homofermentative strain of lactic acid bacteria *L. plantarum* (AIV 755), deposited at Deutsche Sammlung von Mikroorganismen und Zellkulturen under the accession number DSM 4904 on Oct. 20, 1988. The strain can be used in forage preservation because of its favourable effect on preservation. The process of the invention is suitable for use in the preservation of forage, such as grass, e.g., meadow fescue, timothy and cocksfoot.

The process of the present invention for preserving forage is characterized by adding to the forage a *L. plantarum* strain identifiable by the properties mentioned under items I to IV in the present application.

In preserving forage, the bacterium is added in an amount of about $10^5$–$10^7$ cfu/g forage, preferably $10^6$ cfu/g forage. It is preferred to add the bacteria in conjunction with at least one other preservative and possibly in conjunction with at least one other *L. plantarum* strain or other species of lactic acid bacteria. The bacteria and the preservative(s) can be added in a single solution. Suitable preservatives include plant fibre degrading enzymes (such as cellulase), formiate, benzoate, propionic acid and/or acrylic acid. Formiate is preferably used 1,500 g/t forage. The bacterial strain of the invention is identifiable by the properties disclosed under items I to IV in the present application. For instance, the DSM 4904 strain has such properties. The use of these bacteria for preserving forage as well as the forage preserved by the process of the invention also fall within the scope of the invention.

The invention will be described in greater detail hereinbelow.

FIG. 1 shows the plasmid profile of the DSM 4904 strain.

FIG. 2 shows the electrophoresis pictures of the plasmid DNA of the DSM 4904 strain and of cultures isolated at the emptying stage of the silo cut by the BglII restriction enzyme (Boehringer Mannheim GmbH, Mannheim, Penzberg, F.R.G.).

The percentages given are weight/volume percentages for preservative concentrations and weight/weight percentages for the dry matter contents.

Properties of *L. plantarum* strain DSM 4904

I. *L. plantarum* strain isolated from silage and having the following properties:
  gram-positive
  straight, single rod of uniform thickness
  catalase-negative
  homofermentative
  grows at +15° C., no growth at +45° C.
  does not produce ammonium from arginine
  produces L and D lactic acid or specific racemase activity; the amount of L lactic acid about 45% on total amount of lactic acid and the amount of D lactic acid about 55% on total amount of lactic acid; when grown in MRS broth (Difco Laboratories, Detroit, Mich., U.S.A) at 30° C. for 17 hours, total amount of lactic acid is about 2 g/100 ml MRS broth.

Figure 1:
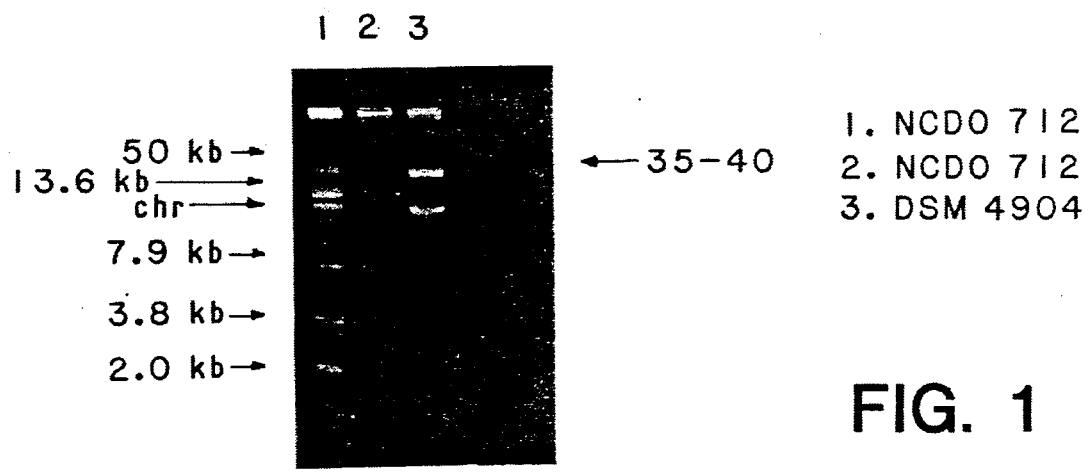
FIGS. 1 and 2 illustrate the description of the bacterial strain.

II. DSM 4904 strain has a single plasmid having rather a high molecular weight (35–40 kb) (FIG. 1).

III. DSM 4904 strain ferments the following sugars or sugar alcohols according to API 50 CH (API System S.A., France):
  L-arabinose, ribose, galactose, D-glucose, D-fructose, D-mannose, mannitol, alpha-methyl-D-mannoside, N-acetylglucosamine, amygdalin, arbutin, esculin, salicin, cellobiose, maltose, lactose, melibiose, sucrose, trehalose, melezitose, D-raffinose, beta-gentiobiose, D-turanose.

IV. Other properties of DSM 4904 strain

A. The strain has formic acid tolerance and at least benzoic acid, acrylic acid and propionic acid tolerance
  in an aqueous solution of sodium formiate ((30%) pH 6.25), for instance, a freeze-dried preparation of the strain remains at least 4 hours at the initial level ($10^9$ cfu/ml)
  grows very well in a MRS broth (pH 6.8) comprising 0.3% benzoic acid, measured in Klett values (Klett-Summerson photoelectric colorimeter, Arthur H. Thomas comp. Philadelphia Pa., U.S.A.). At a benzoic acid concentration of 0.05% in the same broth at pH 4, the growth is still satisfactory. Incubation for 4 days at 30° C.

TABLE 1

| Growth of DSM 4904 strain in MRS broth at different benzoic acid concentrations (4 days 30° C.) | | |
|---|---|---|
| Benzoic acid concentration (%) | pH 6.8 | pH 4.0 |
| | Klett value | |
| 0 | 600 | 500 |
| 0.05 | 600 | 460 |
| 0.1 | 600 | 190 |
| 0.2 | 600 | 15 |
| 0.3 | 550 | 6 |
| 0.4 | 510 | — |
| 0.5 | 470 | — | propionic acid tolerance (MRS broth, pH 4.0) DSM 4904 strain grows well in a broth comprising 0.5% of said acid the strain is acrylic acid tolerant at concentrations 0.1–0.15% (MRS; pH 4.0)

the strain is hexamethyltetramine intolerant

B. Antibiotic sensitivity of the strain

Figure 2:
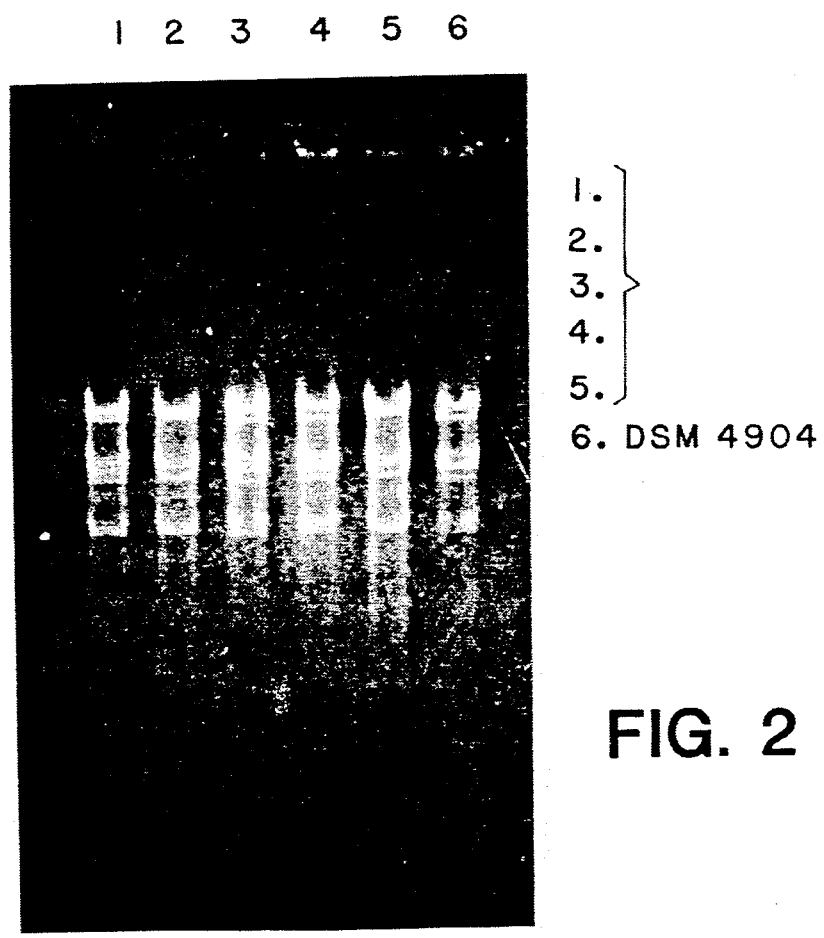

DSM 4904 is fully resistant to the following antibiotics: gentamycin, kanamycin, neomycin, novobiocin, streptomycin, sulfonamides, vancomycin some sensitivity or full sensitivity to the following antibiotics: ampicillin, bacitracin, chloramphenicol, erythromycin, penicillin G, rifamycin, lincomycin, tetracycline, virginiamycin, spectinomycin V. Retention of the strain in silage Retention of DSM 4904 in silage was good. As late as about 5 months after the making of the silage (see Example 2), *L. plantarum* bacteria with characteristic properties identical with those of the DSM 4904 strain were found. They were identical in biochemical reactions and plasmid profiles and were cut identically by BglII (FIG. 2), when growing the strain anaerobically in MRS broth together with the *E. coli* NB strain (isolated from water), the DSM 4904 was able to destroy the coli in 9 days, the amount of DSM 4904 being still $9 \times 10^6$ fcu/ml after 9 days.

VI. Production of cells the strain is grown on a whey-based medium.

The strain is freeze-dried and the freeze-dried preparation can be stored in a refrigerator (−18° C.) for at least 6 months.

VII. Use in forage preservation freeze-dried strain is mixed with water together with other agents used in forage preservation, such as an enzyme and used within four hours from mixing at dose levels of $10^5 \times 10^7$ living cells/g forage. A dosage level of $10^6$ living cells/g forage is to be preferred.

The following examples are illustrative of the invention.

EXAMPLE 1

Chopped grass with a dry matter content of 16.5%, the dry matter containing 16.2% crude protein, 24.2% crude fibre and 12.4% sugar, was ensiled in 10 kg glass silos. The forages were compacted carefully and the silos were sealed air-tightly with a plastic sheet. Additions were made in a single solution by spraying while turning over the forage. Additions made into the test silos were as follows:

A. no preservatives
B. AIV II solution 5 l/t forage
C. DSM 4904 $10^6$ cfu/g forage, enzyme 150 ml/t forage
D. as stated under C and additionally Na-formiate 1,000 g/t forage
E. as stated under C and additionally Na-propionate 2,000 g/t forage and *Pediococcus pentosaceus* ($10^7$ cfu/g).

AIV II solution contains 80% of formic acid and 2% of ortophosphoric acid.

The enzyme is an enzyme preparation degrading plant fibre and containing mainly cellulase as well as other activity, such as hemicellulase.

Results from the preserving trials show that the additions C, D and E had a very favourable effect on the preservability of the silage. Silages C, D and E contain more sugars and less protein degrading products, ammonia, than silages A and B. The high lactic acid/acetic acid ratio in silages C, D and E is indicative of an intense, highly homofermentative lactic acid fermentation.

TABLE 2

| Chemical composition of test silages, ensiling time 60 days | | | | | | |
|---|---|---|---|---|---|---|
| Test silage | pH | Lactic acid | Acetic acid | Butyric acid | Sugar | NH$_3$ g/l |
| | | % on dry basis | | | | |
| A | 3.86 | 10.8 | 2.3 | — | 1.2 | 0.32 |
| B | 3.95 | 4.4 | 1.8 | — | 2.1 | 0.18 |

TABLE 2-continued

Chemical composition of test silages, ensiling time 60 days

| Test silage | pH | Lactic acid | Acetic acid | Butyric acid | Sugar | NH$_3$ g/l |
|---|---|---|---|---|---|---|
| | | % on dry basis | | | | |
| C | 3.72 | 10.4 | 0.9 | — | 2.7 | 0.10 |
| D | 3.77 | 10.0 | 0.8 | — | 3.3 | 0.12 |
| E | 3.80 | 11.0 | 1.2 | — | 2.9 | 0.17 |

Furthermore, the microbiological composition of the test silages shows that strain DSM 4904 has resisted the addition of formiate, and the total amount of lactic acid bacteria has remained on the same level as without formiate addition (TABLE 3).

TABLE 3

Microbiological composition of test silages, ensiling time 60 days

| Test silage | LAB (×10$^6$) | Yeasts (×10$^3$) cfu/g silage | Moulds | CB | Clostridia |
|---|---|---|---|---|---|
| A | 6 | 1.5–510 | <100 | <10 | 3–7 |
| B | 12 | 2–110 | 100–500 | <10 | 3–15 |
| C | 11 | 11–100 | 100–3000 | <10 | 4 |
| D | 7 | 17–110 | 400–1100 | <10 | 3–40 |
| E | 10 | 1900–3900 | <100 | <10 | 3–30 |

(LAB = lactic acid bacteria;
CB = coliform bacteria)

EXAMPLE 2

Grass having a dry matter content of 18.0%, the dry matter containing crude protein 15.3%, crude fibre 27.1% and sugar 10.6%, was chopped in a flail chopper and ensiled in a 500 kg silo. Two parallel silos were provided for each test forage, and the forage was compacted carefully in the silos, whereafter the silos were sealed with a plastic sheet and weighted with vessels filled with water (pressure about 250 kg/m$^2$). The following additions to the forages were made in the chopper:
A. no preservatives
B. AIV II solution 5 l/t forage (see Example 1)
C. DSM 4904 strain 10$^6$ cfu/g forage, enzyme 300 ml/t forage
D. as stated under C and additionally Na-formiate 1,000 g/t forage.

Differences in test silage compositions are similar to those in Example 1 (TABLE 4). When comparing silage C with D, it is to be seen that formiate affected favourably the microbiological composition with respect to the yeasts and moulds present in the silage (TABLE 5).

TABLE 4

Chemical composition of test silages, ensiling time 140 days

| Test silage | pH | Lactic acid | Acetic acid | Butyric acid | Sugar | NH$_3$-N %N |
|---|---|---|---|---|---|---|
| | | % on dry basis | | | | |
| A | 3.92 | 11.2 | 2.6 | — | 0.2 | 10.9 |
| B | 4.15 | 5.2 | 2.0 | 0.9 | 0.5 | 8.7 |
| C | 3.71 | 10.3 | 1.0 | — | 3.3 | 1.8 |
| D | 3.69 | 10.5 | 1.0 | — | 3.7 | 1.8 |

TABLE 5

Microbiological composition of test silages

| Test silage | LAB (×10$^6$) | Yeasts (×10$^3$) cfu/g silage | Moulds | CB | Clostridia |
|---|---|---|---|---|---|
| A | 67–110 | 35–51 | 10–100 | <10 | 14–45 |
| B | 12–55 | 300–440 | 100–200000 | 10–6700 | 450–45000 |
| C | 1–8 | 150–46000 | 10–12000 | 10–60 | <3 |
| D | 1 | 25–170 | <10 | <10 | 3–20 |

The silages were studied for their aerobic resistance and preservability by keeping them at 24° C. and measuring temperature development in each silage. Despite the higher sugar content, silages C and D remained stable for two days (TABLE 6).

TABLE 6

| Test silage | Temperature development in silage (°C.) | | |
|---|---|---|---|
| | 1 day | 2 days | 7 days |
| A | 14 | 18 | 30 |
| B | 10 | 18 | 20 |
| C | 11 | 18 | 34 |
| D | 10 | 18 | 31 |

Formiate improved the stability of silage, and the temperature rise in silage D was slower than in silage C.

EXAMPLE 3

Grass having a dry matter content of 20–22%, the dry matter containing 17.3% crude protein, 24.3% crude fibre and 12.2% sugar, was ensiled in bunker silos of 90 tons. The forages were harvested with a flail chopper and the additions were made in connection with the chopping process. The forages were compacted by trampling with a tractor and covered air-tightly with a plastic sheet. The additions were as follows:
A. no preservatives
B. AIV II solution 5 l/t (cf. Example 1)
C. DSM 4904 strain 10$^6$ cfu/g forage, enzyme 300 ml/t forage
D. as stated under C and additionally Na-formiate 1,500 g/t forage
E. as stated under C and additionally Pediococcus pentosaceus 10$^3$ cfu/g.

As to the quality of silage, the results are consistent with those mentioned in Examples 1 and 2 (TABLE 7).

TABLE 7

Chemical composition of test silages, ensiling time 56 days

| Test silage | pH | Lactic acid | Acetic acid | Butyric acid | Sugar | NH$_3$ g/l |
|---|---|---|---|---|---|---|
| | | % on dry basis | | | | |
| A | 3.89 | 10.1 | 1.6 | 0 | 1.8 | 0.51 |
| B | 4.05 | 1.9 | 0.8 | 0.1 | 10.2 | 0.16 |
| C | 3.87 | 10.7 | 1.6 | 0 | 4.5 | 0.37 |
| D | 3.84 | 10.4 | 1.2 | 0 | 4.0 | 0.30 |

TABLE 7-continued

Chemical composition of test silages, ensiling time 56 days

| Test silage | pH | Lactic acid | Acetic acid | Butyric acid | Sugar | NH$_3$ g/l |
|---|---|---|---|---|---|---|
| | | | % on dry basis | | | |
| E | 3.78 | 10.8 | 0.8 | 0 | 5.3 | 0.21 |

EXAMPLE 4

TABLE 8 shows the pH reduction rate and the L and D lactic acid production rate in the different silages ensiled as stated in Example 2.

TABLE 8 pH reduction and lactic acid production in different silages after an ensiling time of 0 to 14 days (acids % on dry basis)

| Test silage | Assay | Time, days | | | | |
|---|---|---|---|---|---|---|
| | | 0 | 2 | 3 | 7 | 14 |
| A | pH | 5.8 | 5.6 | 4.6 | 4.1 | 4.1 |
| | L lactic acid | 0.1 | 1.4 | 2.7 | 3.9 | 4.7 |
| | D lactic acid | 0.1 | 0.4 | 2.2 | 3.3 | 3.9 |
| | acetic acid | 0.0 | 0.5 | 0.7 | 1.0 | 1.2 |
| B | pH | 4.1 | 4.2 | 4.1 | 4.2 | 4.3 |
| | L lactic acid | 0.1 | 0.0 | 0.1 | 0.1 | 0.4 |
| | D lactic acid | 0.0 | 0.0 | 0.0 | 0.0 | 0.1 |
| | acetic acid | 0.0 | 0.0 | 0.0 | 0.1 | 0.3 |
| C | pH | 5.7 | 3.9 | 3.8 | 3.9 | 3.8 |
| | L lactic acid | 0.1 | 3.1 | 4.1 | 4.4 | 4.7 |
| | D lactic acid | 0.1 | 5.3 | 5.6 | 5.3 | 5.4 |
| | acetic acid | 0.0 | 0.4 | 0.5 | 0.9 | 1.0 |
| D | pH | 5.8 | 4.0 | 3.9 | 3.8 | 3.8 |
| | L lactic acid | 0.1 | 2.5 | 2.8 | 3.9 | 4.0 |
| | D lactic acid | 0.1 | 5.7 | 5.7 | 5.5 | 5.6 |
| | acetic acid | 0.0 | 0.4 | 0.4 | 0.7 | 0.9 |

After two days DSM 4904 strain and enzyme with or without formiate have reduced the pH of silage below 4, which is the desired level for the preserving of the silage. Also the production rate of lactic acid has been high as the total amount of lactic acid after two days was already as high as about 8% on dry basis.

As is typical of DSM 4904 strain, fermentation in the silages has been very homofermentative from the very beginning. The small amount of acetic acid in the silage is indicative of pure fermentation. Moreover, formiate addition has further decreased acetic acid producing fermentation in silage.

EXAMPLE 5a

Grass consisting mainly of timothy was ensiled in 10 kg laboratory silos. The additions were sprayed into the forage with manual spraying, the silage was compacted, weighted and sealed air-tightly. The ensiling time was 60 days. Test results in TABLE 9 show that DSM 4904 strain provides good preserving results. As to the fermentation acids, silage without preservative addition was very similar to DSM 4904 silage whereas DSM 4904 silage had a clearly lower concentration of disadvantageous NH$_3$.

TABLE 9

AIV II solution and DSM 4904 strain in the preservation of grass (AIV II, 5 l/t forage, DSM 4904 strain 10$^6$ cfu/g forage)

| Additions to forage | pH | Lactic acid | Acetic acid | Butyric acid | Sugar | NH$_3$ g/l |
|---|---|---|---|---|---|---|
| | | | % on dry basis | | | |
| No additions | 4.0 | 8.3 | 1.8 | 0 | 1.3 | 0.39 |

TABLE 9-continued

AIV II solution and DSM 4904 strain in the preservation of grass (AIV II, 5 l/t forage, DSM 4904 strain 10$^6$ cfu/g forage)

| Additions to forage | pH | Lactic acid | Acetic acid | Butyric acid | Sugar | NH$_3$ g/l |
|---|---|---|---|---|---|---|
| | | | % on dry basis | | | |
| AIV II | 4.1 | 3.6 | 0.9 | 0 | 7.1 | 0.24 |
| DSM 4904 strain | 3.9 | 7.5 | 1.8 | 0 | 1.4 | 0.12 |

EXAMPLE 5b

Grass consisting mainly of timothy was ensiled in bunker silos of about 10 tons. Forages were harvested with a forage harvester and the preservative was added to the forage in connection with the harvesting. The silos were sealed air-tightly with a plastic sheet and weighted with water weights.

As appears from TABLE 10, silage with enzyme addition was very similar to that without preservative addition. When comparing the results shown in TABLES 9 and 10, it is to be seen that the silage with enzyme addition is clearly inferior to that with DSM 4904 addition with respect to the NH$_3$ concentration.

TABLE 10

Effect of cellulase enzyme on the fermentation of grass, ensiling time 140 days

| Preservative | pH | Lactic acid | Acetic acid | Butyric acid | Sugar | NH$_3$ g/l |
|---|---|---|---|---|---|---|
| | | | % on dry basis | | | |
| No preservative | 3.89 | 7.4 | 1.0 | 0 | 2.7 | 0.77 |
| Enzyme | 3.82 | 9.5 | 0.9 | 0 | 3.1 | 0.59 |

EXAMPLE 6

Grass consisting mainly of timothy was ensiled in 10 kg laboratory silos as described in Example 5.

TABLE 11

Effect of Na propionate on silage fermentation

| Additions to forage | pH | Lactic acid | Acetic acid | Butyric acid | Sugar acid | NH$_3$ g/l | LAB cfu/g ×10$^6$ |
|---|---|---|---|---|---|---|---|
| | | | % on dry basis | | | | |
| DSM 4904 + enzyme | 3.8 | 12.1 | 1.3 | 0 | 2.4 | 0.15 | 9.5 |
| DSM 4904 + enzyme + 0.2% Na-propionate | 3.8 | 12.6 | 1.1 | 0 | 2.9 | 0.13 | 160 |

Na propionate did not affect adversely the amount of lactic acid bacteria (LAB), whereas the quality of fermentation (lactic acid/acetic acid ratio; amount of NH$_3$) was improved (TABLE 11).

EXAMPLE 7

About 45 tons of grass mainly consisting of timothy and meadow fescue was ensiled in a bunker silo. The grass was chopped with a forage harvester, into which the additions were made during harvesting. The grass was compacted in the silo with a tractor, covered airtightly with a plastic sheet, and weighted.

TABLE 12

| Additions to forage | pH | Lactic acid | Acetic acid | Butyric acid | Sugar | NH$_3$ g/l |
|---|---|---|---|---|---|---|
| | | | % on dry basis | | | |
| DSM 4904 + enzyme | 3.9 | 10.7 | 1.6 | 0 | 4.5 | 0.37 |
| DSM 4904 + enzyme + 0.05% SB | 3.9 | 10.3 | 1.5 | 0 | 3.0 | 0.37 |
| DSM 4904 + enzyme + 0.1% SB | 3.8 | 11.1 | 1.1 | 0 | 4.7 | 0.24 |

(SB = sodium benzoate).

Sodium benzoate did not affect adversely the amount of lactic acid bacteria (LAB). In all silages, the amount of lactic acid bacteria varied between $10^6$ and $10^8$ cfu/g. The benzoate treatment reduced considerably the amount of yeasts. Without benzoate, the amount of yeasts was 100 cfu/g. Silage treated with benzoate did not contain yeasts. The quality of fermentation was still better on a dosage level of 0.1% sodium benzoate (TABLE 12).

We claim:

1. A process of preserving forage consisting essentially of adding to the forage as fermentative microorganism an effective amount of *Lactobacillus plantarum* DSM 4904 to preserve said forage.

2. A process of preserving forage according to claim 1, wherein the *Lactobacillus plantarum* DSM 4904 is added in an amount of about $10^5$–$10^7$ cfu/g forage.

3. A process of preserving forage according to claim 1, wherein the *Lactobacillus plantarum* DSM 4904 is added in an amount of $10^6$ cfu/g of forage.

4. A process of preserving forage according to claim 1, wherein the forage is grass.

5. A process of preserving forage according to claim 1, wherein at least one other preservative is added to the forage.

6. A process of preserving forage of according to claim 5 wherein the *Lactobacillus plantarum* DSM 4904 and the other preservative are added in a single solution.

7. A process of preserving forage according to claim 5, wherein the other preservative is a plant fiber degrading enzyme.

8. A process of preserving forage according to claim 7, wherein said plant fiber degrading enzyme is cellulase.

9. A process of preserving forage to claim 5, wherein the other preservative contains an organic acid or a salt thereof.

10. A process of preserving a forage according to claim 9, wherein said preservative is selected from the group consisting of sodium formiate, sodium benzoate, propionic acid and acrylic acid.

11. A process of preserving forage according to claim 10, wherein the sodium formiate is added in an amount of about 1,500 g/t forage.

12. A process of preserving forage according to claim 1, wherein at least one other *Lactobacillus plantarum* strain or a strain of another species of lactic acid bacteria is added to the forage.

13. A process of preserving forage according to claim 12, wherein at least one other preservative is added to the forage.

14. A process for preserving forage according to claim 13, wherein said forage is grass.

15. A biologically pure culture off bacterial strain *L. plantarum* DSM 4904 wherein said culture is capable of use in enhancing the preservation of forage.

16. A forage which consists essentially of said forage and contains *Lactobacillus plantarum* DSM 4904 in an amount effective for preserving said forage.

17. A forage consisting essentially of *Lactobacillus plantarum* DSM 4904 in an effective amount to pressure forage.

18. A forage preservative according to claim 17, containing also, at least one plant fiber degrading enzyme.

19. A forage preservative according to claim 18, containing also at least one organic acid or a salt thereof.

20. A forage preservative according to claim 19, containing also at least one other *Lactobacillus plantarum* strain or strain of lactic acid bacteria.

21. A process for preserving forage consisting essentially of adding as fermentative microorganism, an effective amount of *Lactobacillus plantarum* DSM 4904; and adding a plant fiber degrading enzyme, at least one other preservature, and at least one other *Lactobacillus plantarum* strain or a strain of another species of lactic and bacteria.

* * * * *

UNITED STATES PATENT AND TRADEMARK OFFICE
CERTIFICATE OF CORRECTION

PATENT NO. : 5,053,233

DATED : October 1, 1991

INVENTOR(S) : Jouko J. Setala, et al.

It is certified that error appears in the above-identified patent and that said Letters Patent is hereby corrected as shown below:

Claim 9, col. 10, line 4, "forage to claim 5" should read --forage according to claim 5--.

Claim 15, col. 10, line 23, "culture off bacterial" should read --culture of bacterial--.

Claim 17, col. 10, lines 30-31, "to pressure forage" should read --to preserve forage--.

Signed and Sealed this

Fifteenth Day of September, 1992

Attest:

DOUGLAS B. COMER

*Attesting Officer*   Acting Commissioner of Patents and Trademarks

UNITED STATES PATENT AND TRADEMARK OFFICE
CERTIFICATE OF CORRECTION

PATENT NO. : 5,053,233
DATED : October 1, 1991
INVENTOR(S) : Jouko J. Setala, et. al.

It is certified that error appears in the above-identified patent and that said Letters Patent is hereby corrected as shown below:

Column 10, lines 46-47, "lactic and bacteria" should read -- lactic acid bacteria--.

Signed and Sealed this

Twenty-ninth Day of December, 1992

Attest:

DOUGLAS B. COMER

*Attesting Officer*  Acting Commissioner of Patents and Trademarks